(12) United States Patent
Hara (10) Patent No.: US 8,157,379 B2
(45) Date of Patent: Apr. 17, 2012

(54) PERIMETER AND METHOD OF CONTROLLING PERIMETER

(75) Inventor: Takuya Hara, Shizuoka-ken (JP)

(73) Assignee: Kowa Company, Ltd., Aichi (JP)

( * ) Notice: Subject to any disclaimer, the term of this patent is extended or adjusted under 35 U.S.C. 154(b) by 87 days.

(21) Appl. No.: 12/868,174

(22) Filed: Aug. 25, 2010

(65) Prior Publication Data

US 2011/0234980 A1 Sep. 29, 2011

(30) Foreign Application Priority Data

Mar. 29, 2010 (JP) ................................ 2010-074729

(51) Int. Cl.
*A61B 3/02* (2006.01)
(52) U.S. Cl. ........................ 351/224; 351/226
(58) Field of Classification Search ........... 351/200–246
See application file for complete search history.

(56) References Cited

U.S. PATENT DOCUMENTS

| | | | | |
|---|---|---|---|---|
| 7,309,129 B2* | 12/2007 | Suzuki | ......................... | 351/224 |
| 7,377,646 B2* | 5/2008 | Suzuki | ......................... | 351/224 |
| 7,942,528 B2* | 5/2011 | Hara | ........................... | 351/224 |
| 7,993,002 B2* | 8/2011 | Tsuta | ........................... | 351/226 |

FOREIGN PATENT DOCUMENTS

JP 2002-272685 9/2002

\* cited by examiner

*Primary Examiner* — Mohammed Hasan (74) *Attorney, Agent, or Firm* — Duane Morris LLP (57) ABSTRACT

In a perimeter, luminance judging means measures a sensitivity of an examinee, sensitivity deviation computing means obtains a sensitivity deviation, means for computing ratio to p value obtains a ratio to p value, and means for adding ratios to p value adds ratios to p value of respective measurement positions. The sensitivity deviation at the position where sensitivity dispersion is large is low evaluated and the sensitivity deviation at the position where the sensitivity dispersion is small is highly evaluated. Then, an element of the position where the sensitivity was changed can be also considered in a graph showing test results of perimetry periodically conducted with time.

5 Claims, 7 Drawing Sheets

PERIMETER AND METHOD OF CONTROLLING PERIMETER

CROSS REFERENCE TO RELATED APPLICATION

The present disclosure relates to subject matter contained in Japanese patent application No. 2010-74729 filed on Mar. 29, 2010, the disclosure of which is expressly incorporated herein by reference in its entirety.

BACKGROUND OF THE INVENTION

This invention relates to a perimeter for measuring a visual field of an examinee in such a state that the examinee fixates a fixation target and a method of controlling the perimeter.

BACKGROUND ART

When suffering from an ophthalmic disease, such as glaucoma and diabetic retinopathy, it is known that a person has a visual field contraction or a visual field defect. For these reasons, perimeters having various structures have been proposed as devices for finding such diseases (see Japanese patent application the publication number of which is 2002-272685).

Figure 5:
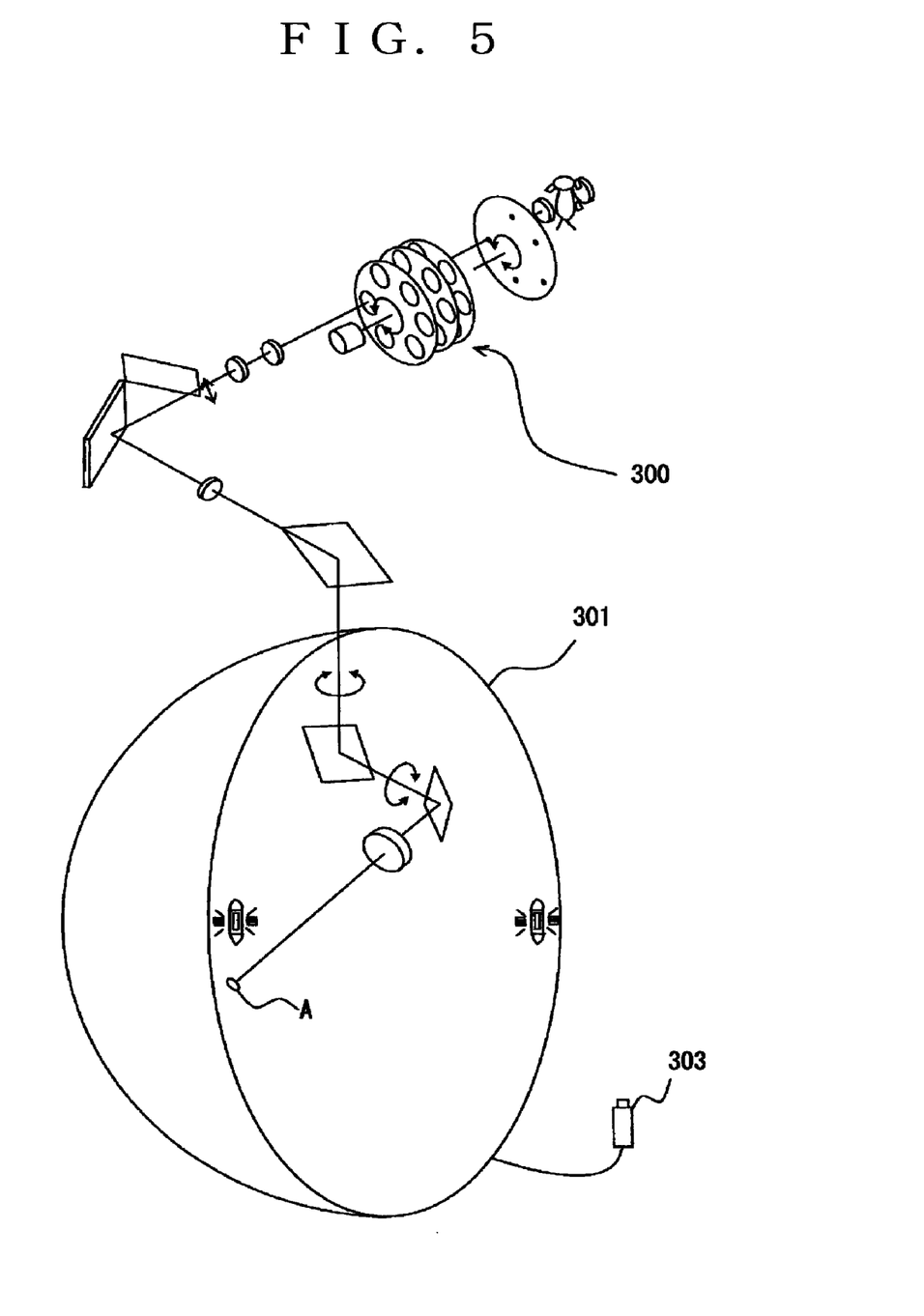
FIG. 5 is a typical view of an example of a structure of the perimeter.

FIG. 5 is a typical view showing a structure of a perimeter. In FIG. 5, a reference numeral 300 denotes a projection optical system for projecting stimuli A, and a reference numeral 301 denotes a visual field dome in the shape of a semi-sphere for projecting stimuli A thereon. And, a reference numeral 303 denotes a response switch to be operated by an examinee.

When starting the perimeter in such a state that an examinee fixates a fixation target (a center point of the visual field dome 301, for example) inside the visual field dome 301, the projection optical system 300 successively displays stimuli A at various positions of the visual field dome 301. If the examinee do not perceive the stimulus A, luminance of the stimuli is gradually raised in order to obtain the luminance at which the examinee can perceive the stimulus.

In order to know a progress of an ophthalmic disease, such as glaucoma, it is necessary to periodically conduct the above-mentioned perimetry and to grasp changes with time of test results. Then, the following method has been adopted. That is, the method is comprised of (1) to conduct the above-mentioned perimetry on the examinee and to obtain the luminance of the stimulus which the examinee can perceive for two or more positions (stimulus presentation position), (2) to obtain a difference (total deviation) between a normal value (that is, a representative value of the luminance of the stimulus to be perceived with a normal eye, which is mentioned in detail later) and test results (that is, the luminance of the stimulus which the examinee actually perceived) for each position where the stimulus should be presented, (3) to obtain an average value (MD value: Mean Deviation value) obtained by dividing the total deviation obtained for each position where the stimulus should be presented by the number of positions where the stimulus should be presented, and (4) to show the changes with time of the MD value in a graph.

Figure 6:
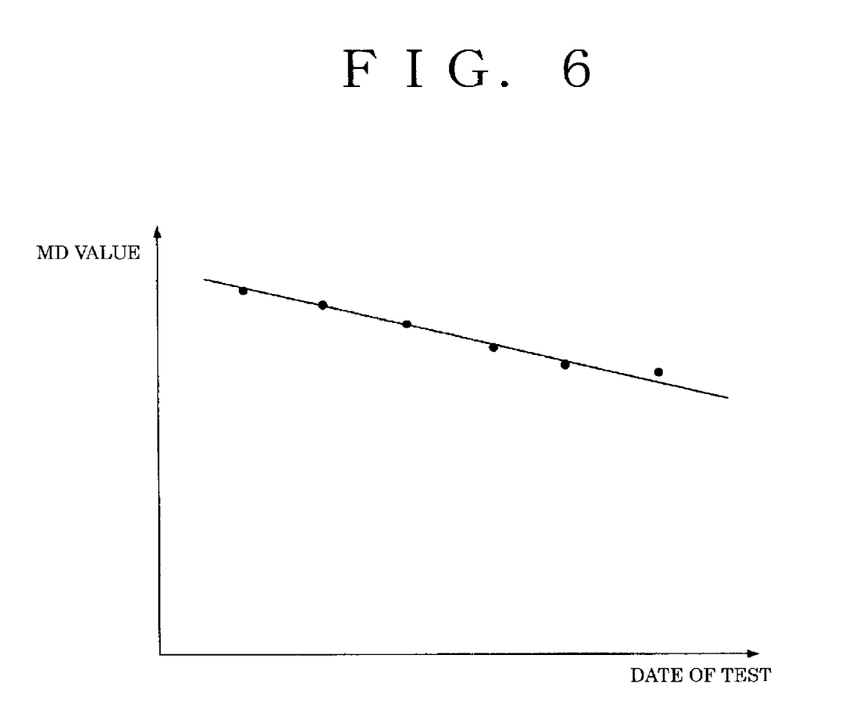
FIG. 6 is a view showing an example of a change of MD value with time.

FIG. 6 is a view (graph) showing the changes of the MD value with time, and a longitudinal axis shows the MD value and a transverse axis shows time (that is, a date when each test is conducted). If sensitivity (that is, the luminance of the stimulus that can be perceived) of some examinee in some position (the position where the stimulus should be presented) in some test is lowered by 2 dB in comparison with one in the last test for example, the total deviation in the position is also changed by 2 dB and the MD value is changed thereby. Then, the progress of the disease is grasped by the change of the MD value.

The other method is to obtain a PSD value (standard deviation of the above-mentioned total deviation) and to know changes thereof with time in order to grasp the progress of the disease.

Figure 7:
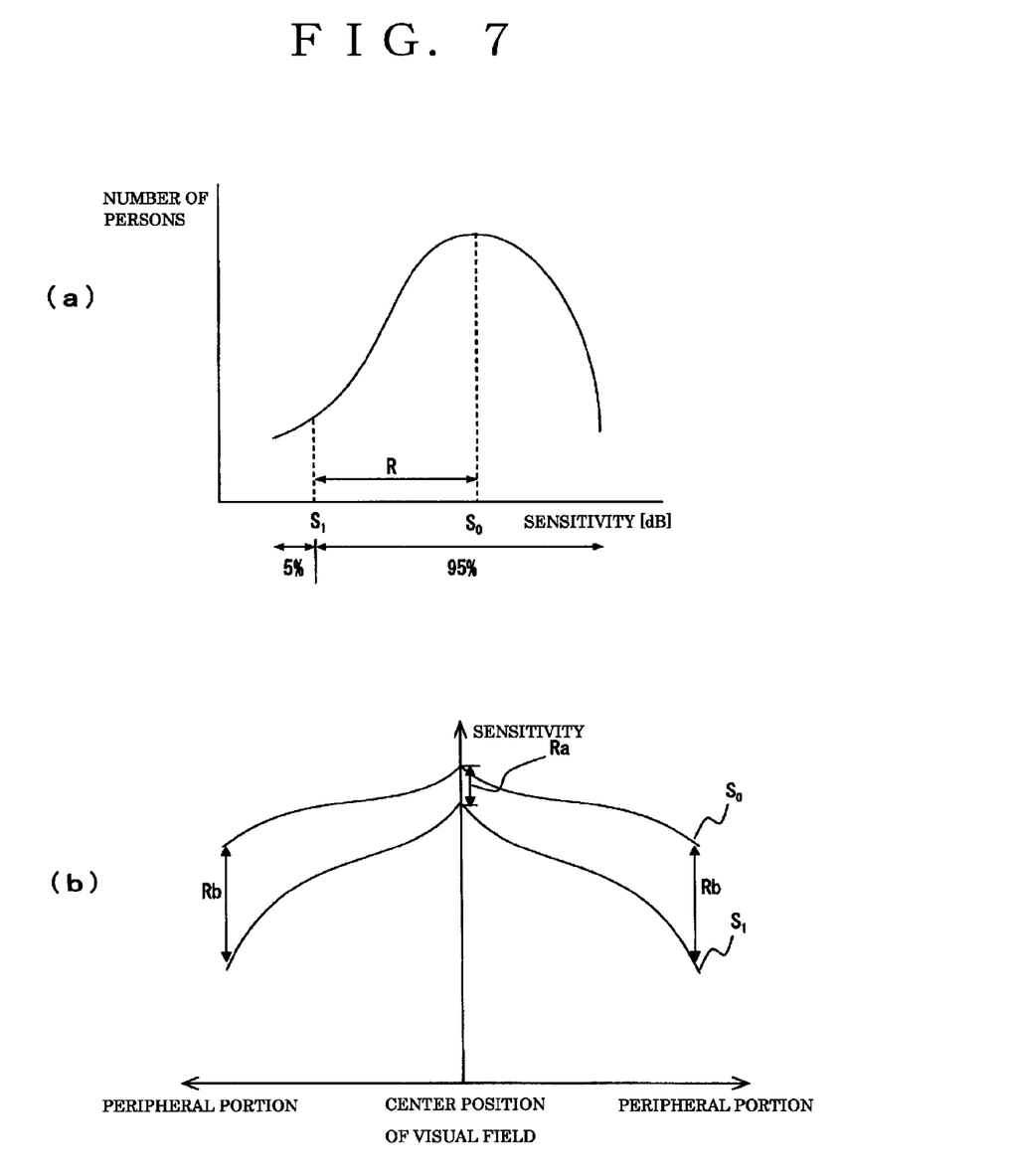
FIG. 7(a) is a view showing an example of the characteristic curve obtained by conducting perimetry on many (two or more) persons having normal eyes.
FIG. 7(b) is a view showing a relation between a position in a visual field and sensitivity.

The sensitivity varies widely, depending on persons even if the persons have normal eyes. That is, the sensitivity of a normal eye of a person in some position may be different from the sensitivity of a normal eye of the other person in the position due to an individual difference. Even if the sensitivity of many persons having normal eyes in a predetermined position is measured, measurement result may not be the same but different. For example, the measurement result shows a distribution (characteristic curve) as shown in FIG. 7($a$). In a graph in FIG. 7($a$), a transverse axis shows the sensitivity and a longitudinal axis shows number of persons. If the sensitivity showing a peak in such a characteristic curve (the sensitivity shown with $S_0$ in FIG. 7($a$)) is defined as "a normal value", and the sensitivity of a boundary between 95 percent of measured persons and 5 percent of the measured persons, such as the sensitivity wherein 95 percent of the measured persons enter a right side range (that is, good sensitivity side) and the remaining 5 percent of the measured persons enter a left side range (that is, poor sensitivity side), is defined as "p value=5%, and a range R between the normal value $S_0$ and p value=5% (see $S_1$) is defined as "sensitivity dispersion range", such characteristic curve changes depending on measurement positions. Then, the normal value $S_0$, p value=5% (see $S_1$) and the sensitivity dispersion range R also change depending on the measurement positions (positions in the visual field). Such changes have an inclination as shown in FIG. 7($b$), and the sensitivity dispersion range is the smallest in the central portion of the visual field (see Ra), and becomes bigger as a peripheral portion of the visual field draws close (see Rb). For this reason, if the sensitivity is lowered by 2 dB, there is a big problem incase where the position is in the central portion of the visual field (the central portion of the visual field where the sensitivity dispersion range is small), but it is not possible to make judgments only with the test results in a case where the position is in the peripheral portion of the visual field (the peripheral portion of the visual field where the sensitivity dispersion range is large).

However, the above-mentioned MD value and the PSD value only show the same changes with time in both cases where the sensitivity is lowered by 2 dB in the central portion and the peripheral portion of the visual field. For this reason, there is such a problem that it is not possible to make judgments as to whether the changes with time are considered to be important or not. Normal life is hindered if the sensitivity in the central portion of the visual field is lowered. Then, it is necessary to take some proper medical step if the sensitivity in the central portion of the visual field is lowered. But, it is difficult to make such judgments only with the changes with time.

An object of the invention is to provide a perimeter for solving the above-mentioned problems and a method of controlling the perimeter.

SUMMARY OF THE INVENTION

Figure 1:
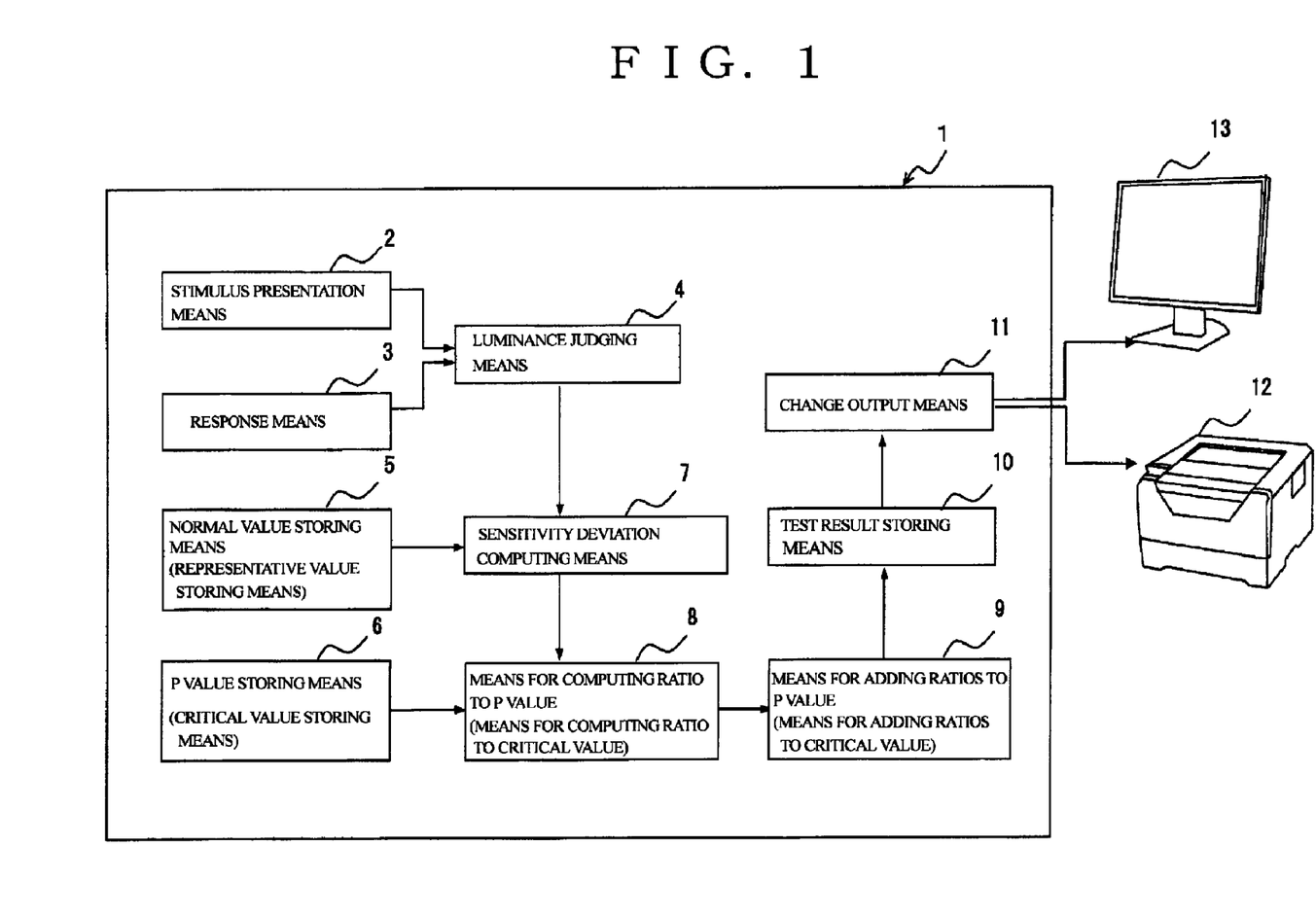
FIG. 1 is a block diagram that shows an example of a structure of a perimeter according to the invention.

A first aspect of the invention is a perimeter as shown in FIG. 1, for example, for testing a visual field of an examinee in such a state the examinee fixates a predetermined fixation target, comprising:

stimulus presentation means for presenting a stimulus having predetermined luminance in order at a plurality of positions where stimulus should be presented in a periphery of said fixation target;

response means through which an examiner or the examinee inputs response signals showing that the examinee actually perceived the presented stimulus;

luminance judging means for judging said luminance of said stimulus perceived by the examinee for each position where said stimulus should be presented based upon signals from said stimulus presentation means and said response means;

representative value storing means for storing "a representative value of the luminance of the stimulus to be perceived with normal eyes" statistically obtained in perimetry that is conducted on a plurality of persons having normal eyes as data in connection with each position where the stimulus should be presented;

critical value storing means for storing "a critical value that shows a boundary of the luminance of the stimulus perceived by a predetermined rate of normal eyes" statistically obtained in perimetry that is conducted on a plurality of persons having normal eyes as data in connection with each position where the stimulus should be presented;

sensitivity deviation computing means for computing sensitivity deviation that is a difference between a value in connection with the luminance of the stimulus perceived by the examinee and said representative value for each position where the stimulus should be presented based upon said signals from said luminance judging means and said data of said representative value storing means;

means for computing ratio to critical value which computes "a ratio to critical value" that is a ratio between a critical value stored in said critical value storing means and said sensitivity deviation computed by said sensitivity deviation computing means for each position where the stimulus should be presented; and means for adding ratios to critical value, which computes a total value of said ratios to critical value computed for each position where the stimulus should be presented or an average value obtained by dividing said total value by number of positions where the stimulus should be presented.

A second aspect of the invention is the perimeter, wherein said representative value is a value determined from a characteristic curve that shows a relation between "the luminance of the stimulus" obtained by conducting perimetry on a plurality of persons having normal eyes and "number of persons who actually perceived the stimulus having the luminance", and is the value based upon the luminance of the stimulus perceived by the most persons, a value based upon an average value obtained by dividing the perceived luminance by a number of said persons, or a value based upon the luminance of the stimulus perceived by almost middle rank of person when said persons are ranked based upon the perceived luminance.

The third aspect of the perimeter, further comprising:

test result storing means for storing said total value or said average value computed by said means for adding ratios to critical value as well as examinee ID for identification of the examinees; and change output means for outputting changes with time in the total value or the average value of the examinee.

A fourth aspect of the invention is a method of controlling a perimeter, comprising:

a step of presenting a stimulus having predetermined luminance in order to a plurality of positions where the stimulus should be presented through stimulus presentation means;

a step of judging the luminance of the stimulus perceived by the examinee for each position where the stimulus should be presented through luminance judging means based upon response signals showing that the examinee has perceived the presented stimulus and signals from the stimulus presentation means;

a step of computing sensitivity deviation which is a difference between a value regarding the luminance of the stimulus perceived by the examinee and the representative value through sensitivity deviation computing means for each position where the stimulus should be presented based upon "a representative value of the luminance of the stimulus to be perceived with normal eyes" that is stored in representative value storing means as data in connection with each position where each stimulus should be presented and the signals from the luminance judging means;

a step of computing "a ratio to critical value" that is the ratio between "a critical value that is a boundary of the luminance of the stimulus perceived by a predetermined rate of normal eyes" that is stored in critical value storing means as data in connection with each position where the stimulus should be presented and the sensitivity deviation computed by the sensitivity deviation computing means for each position where the stimulus should be presented through means for computing ratio to critical value; and a step of computing a total value of ratios to critical value computed for respective positions where the stimulus should be presented or an average value obtained by dividing the total value by number of positions where the stimulus should be presented through means for adding ratios to critical value.

A fifth aspect of the invention is the method of controlling the perimeter, further comprising:

a step of storing the total value or the average value that is computed by means of adding ratios to critical value through the test result storing means as well as an examinee ID for identification of each examinee, and a step of outputting change of the total value or the average value of the examinee with time through change output means.

According to these aspects of the invention, as shown in FIG. 7(b), a sensitivity dispersion region is different, depending on the positions where sensitivity is measured (that is, the position where the stimulus should be presented), and has an inclination to be the smallest in a center position of the visual field and to become bigger as the peripheral portion of the visual field draws close. The above-mentioned critical value (in claims 1 to 7) is the value in connection with "change of the sensitivity dispersion region", and "the ratio to critical value" and "the total value or the average value of the ratio to critical value" is the value adding an element, "change of the sensitivity dispersion region" thereto. In other words, in a case where the sensitivity deviation at a position where critical value=5% is −10 dB, such as a peripheral portion of the visual field, is lowered by 1 dB, the ratio to critical value (=sensitivity deviation/critical value) becomes −0.1. In a case where the sensitivity deviation at a position where critical value=5% is −2 dB, such as a central portion of the visual field is lowered by 1 dB, the ratio to critical value (=sensitivity deviation/critical value) becomes −0.5. Even if a degree of lowering the sensitivity deviation is the same, the numeral value (absolute value) becomes bigger if it is lowered at the central portion of the visual field and the total value or the average value of the ratio to critical value is widely changed. Then, it is possible to judge as to whether it is important or not by watching the changes with time of the total value or the average value of the ratio to critical value even if the same amount of sensitivity deviation is lowered.

DESCRIPTION OF THE PREFERRED EMBODIMENTS

An embodiment of the invention is mentioned, referring to appended FIGS. 1 to 4.

Figure 2:
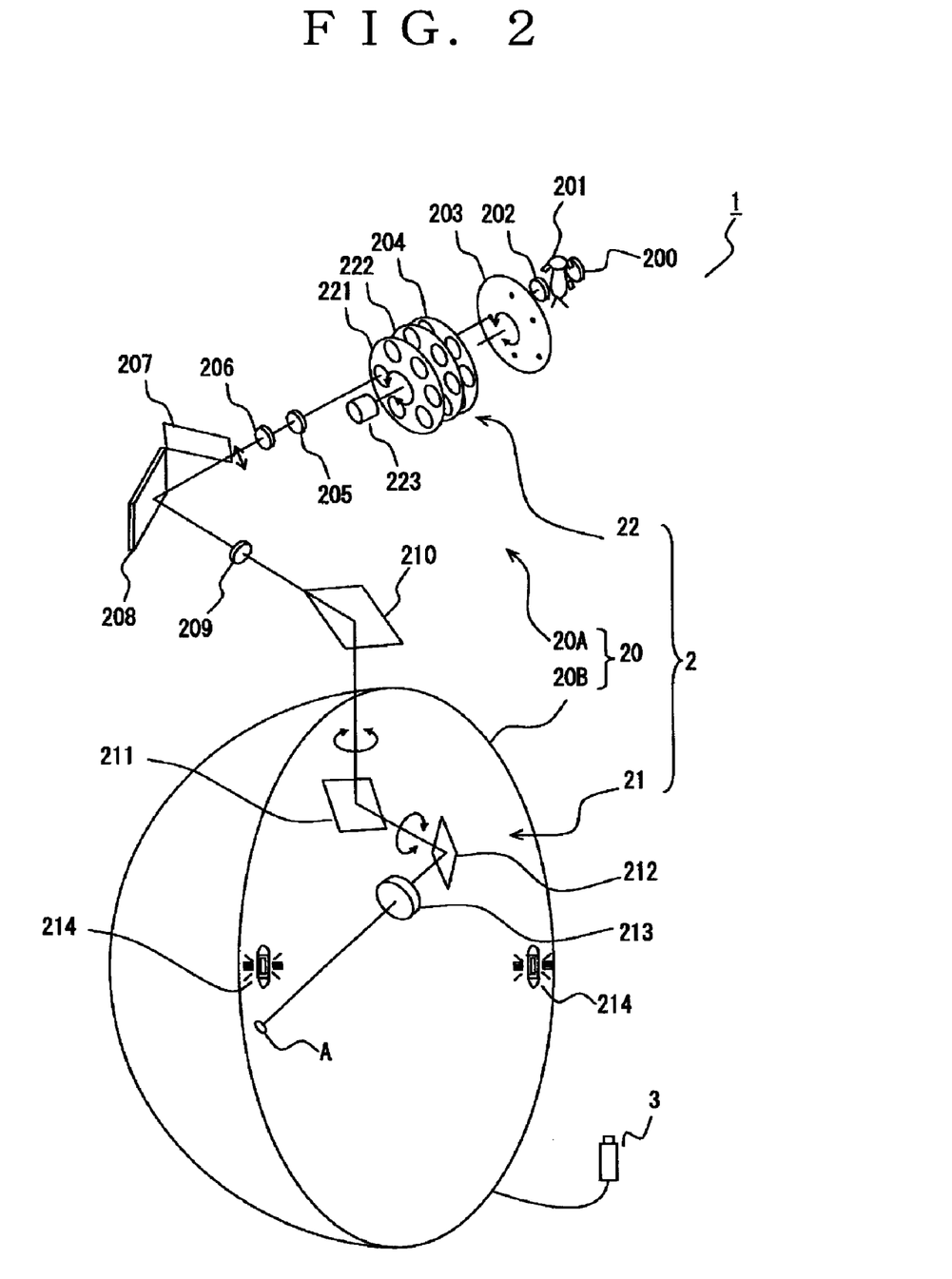
FIG. 2 is a typical view showing an example of the structure of the perimeter (especially, a portion of stimulus presentation means) according to the invention.

A perimeter according to the invention is constructed so as to test a visual field of an examinee in such a state that the examinee fixates a predetermined fixation target, such as a center point of a visual field dome 20B shown in FIG. 2). Such a perimeter is exemplarily shown with a reference number 1 in FIG. 1 or FIG. 2, and has stimulus presentation means 2 (will be mentioned in detail) for presenting a stimulus A having predetermined luminance at a plurality of peripheral positions of the fixation target ("the position where the stimulus should be presented" in the specification) in order.

Such an perimeter 1 is provided with response means 3, such as a push switch. If the examinee who perceived the presented stimulus A (or an examiner watching a response of the examinee) operates the response means 3, response signals (that is, signals showing that the examinee actually perceived the presented stimulus) can be inputted into the perimeter 1 (concretely speaking, into luminance judging means 4).

The perimeter 1 according to the invention has luminance judging means 4 for judging luminance of the stimulus which the examinee perceived for each position where stimulus should be presented based upon signals from the stimulus presentation means 2 and the response means 3. Such luminance judging means 4 may output a difference between "luminance that is some standard (standard luminance)" and "measurement luminance (that is, the luminance of the stimulus which the examinee actually perceived)".

Figure 3:
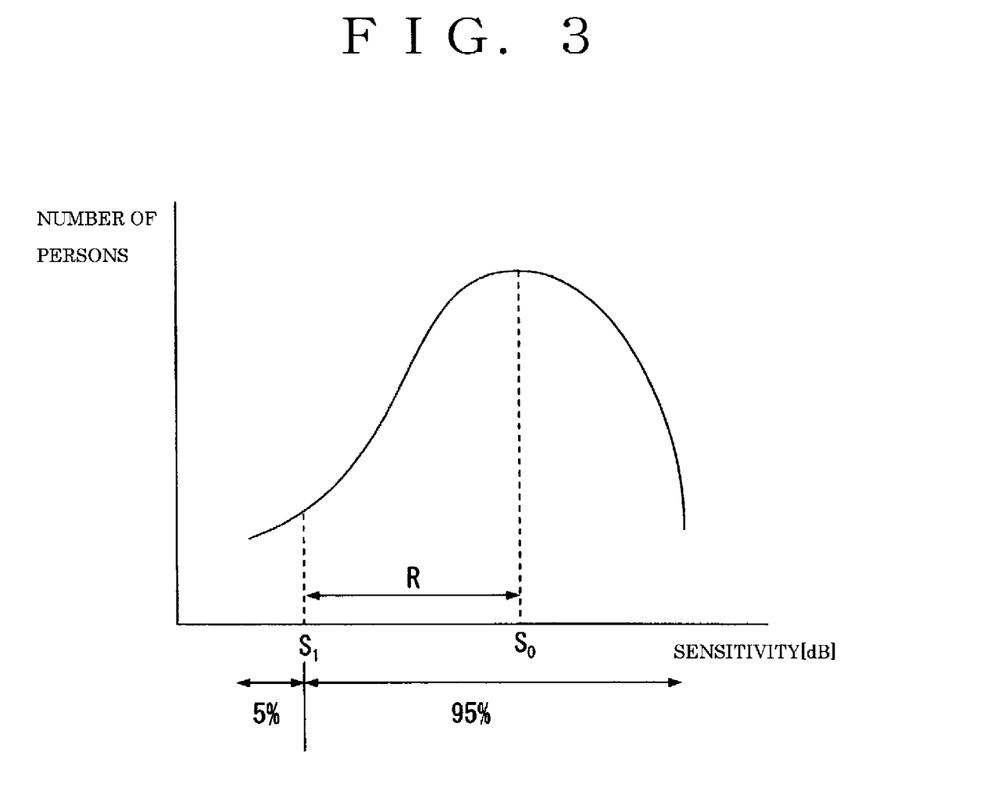
FIG. 3 is a view of an example of a characteristic curve obtained by conducting perimetry on many (two or more) persons having normal eyes.

There is an individual difference between persons having normal eyes in the luminance of the stimulus that can be perceived. Such an individual difference appears as a characteristic curve as shown in FIG. 3 if perimetry is conducted on many (a plurality of) persons having normal eyes and data are collected. A transverse axis of FIG. 3 shows sensitivity (that is, a value in connection with the luminance of the presented stimulus, and concretely speaking, a difference between the standard luminance and the measurement luminance) and a longitudinal axis shows a number of persons who have perceived the stimulus. In the specification, any one of (1) a value based upon the luminance of the stimulus which the most persons have perceived (see a reference mark $S_0$) (2) a value based upon an average value obtained by dividing the perceived luminance by number of persons, (3) a value based upon the luminance of the stimulus which an almost middle rank of person have perceived if the persons who have perceived the stimulus are ranked based upon the perceived luminance (for example, the sensitivity of the $50^{th}$ person from the person having the best sensitivity, if perimetry is conducted on a hundred of persons), and (4) a value that is the other standard excluding the above-mentioned values, such as the sensitivity of the n-th person from the upper ranked person, is defined as "a normal value (corresponds to "a representative value" in claims)". In other words, "the normal value (the representative value) of the luminance of the stimulus to be perceived by normal eyes" is statistically obtained in the above-mentioned way in the invention. Since the above-mentioned characteristic curve is obtained by presenting the stimulus to the same position (the same position where the stimulus should be presented) between many persons, the other characteristic curve is obtained in the other position where the stimulus should be presented. So, the normal value (the representative value) is also different, depending on the position where the stimulus should be presented. The perimeter 1 according to the invention has normal value storing means 5 (representative value storing means) for storing the normal value for each position where the stimulus should be presented as data.

On the other hand, the sensitivity through which number of measured persons can be distributed at a constant rate (see $S_1$ in FIG. 3) in the above-mentioned characteristic curve is referred to as "a critical value (p value)" in the specification. For example, a critical value $S_1$ as shown in FIG. 3 shows such a sensitivity that 95 percent of the persons are within a right side range (good sensitivity side) and 5 percent of the persons are within a left side region (poor sensitivity side). In the specification, such a p value (the p value wherein 5 percent of the persons are within the poor sensitivity side) is referred to as "p value=5%, if necessary. In other words, if the sensitivity in p value=5% is 3 dB, 95 percent of the persons can perceive the stimulus brighter than 3 dB. The p value is different, depending on the position where the stimulus should be presented, but the perimeter 1 according to the invention has p value storing means 6 (critical value storing means) for storing p values for respective positions where the stimulus should be presented as data.

On the other hand, the perimeter according to the invention has sensitivity deviation computing means for computing a sensitivity deviation for each position where the stimulus should be presented from signals from the luminance judging means 4 and data of the normal value storing means 5 (that is, the normal value for each position where the stimulus should be presented). Such a sensitivity deviation is a concept including a total deviation and a pattern deviation, and means a difference between a value regarding the luminance of the stimulus which the examinee actually perceived (the luminance itself or the above-mentioned sensitivity) and the above-mentioned normal value (the luminance itself or the above-mentioned sensitivity).

Furthermore, the perimeter 1 according to the invention has means for computing ratio to p value (means for computing ratio to critical value), which computes "ratio top value (corresponds ratio to critical value in claims)" that is a ratio between the p value and the sensitivity deviation for each position where the stimulus should be presented. Such means for computing ratio to p value 8 may obtain a ratio of "p value ratio/sensitivity deviation or may obtain its inverse number (that is, the ratio of "sensitivity deviation/p value ratio"). In a case where p value=5% is 3 dB in some position where the stimulus should be presented and the sensitivity deviation of some examinee in the position where the stimulus should be presented is 1.5 dB, the computed ratio to p value is 0.5 (or its inverse number 2). The ratio computed through means for computing ratio to p value 8 may not be such a ratio (the ratio in a strict meaning), but may be "some function between the sensitivity deviation and the p value" that changes due to the change of the sensitivity deviation.

In addition, the perimeter 1 according to the invention has means for adding ratios to p value (means for adding ratios to critical value) 9, which computes a total value of ratios top value computed for respective positions where the stimulus should be presented or an average value obtained by dividing the total value by the number of the positions where the stimulus should be presented. The means for adding ratios to p value 9 includes means for obtaining the total value and the average value and also includes means for obtaining some value equivalent thereto. If the ratio to p value in each position where the stimulus should be presented is $B_1$, $B_2$ and $B_3$, the concept of "the total value of the ratios to p value or the average value obtained by dividing the total value by the number of the positions where the stimulus should be presented" also includes some value obtained by using the ratio to p value of each position where the stimulus should be presented that is influenced by the change of any of the ratio to p value as well as the total value of the ratios to p value "$B_1+B_2+B_3+\ldots$" and the average value of the ratios to p value "$(B_1+B_2+B_3+\ldots)/n$" For example, a value obtained by multiplying the ratio to p value by coefficient for weight $C_1, \ldots$, such as $C_1*B_1+C_2*B_2+C_3*B_3+\ldots$ and $(C_1*B_1+C_2*B_2+C_3*B_3+\ldots)/n$, is also included therein.

As shown in FIG. 7(b), a sensitivity dispersion region is different, depending on the positions where sensitivity is measured (that is, the position where the stimulus should be presented), and has an inclination to be the smallest in a center position of the visual field and to become bigger as the peripheral region of the visual field draws close. The above-mentioned p value (the critical value) is the value in connection with "change of the sensitivity dispersion region", and "the ratio to p value" and "the total value or the average value of the ratio to p value" is the value adding an element, "change of the sensitivity dispersion region" thereto. In other words, in a case where the sensitivity deviation at a position where p value=5% is −10 dB, such as a peripheral portion of the visual field, is lowered by 1 dB, the ratio to p value (=sensitivity deviation/p value) becomes −0.1. In a case where the sensitivity deviation at a position where p value=5% is −2 dB, such as a central portion of the visual field is lowered by 1 dB, the ratio to p value (=sensitivity deviation/p value) becomes −0.5. Even if a degree of lowering the sensitivity deviation is the same, the numeral value (absolute value) becomes bigger if it is lowered at the central portion of the visual field and the total value or the average value of the ratio to p value is widely changed. Then, it is possible to judge as to whether it is important or not by watching changes of the total value or the average value of the ratio to p value with time even if the same amount of sensitivity deviation is lowered.

Figure 4:
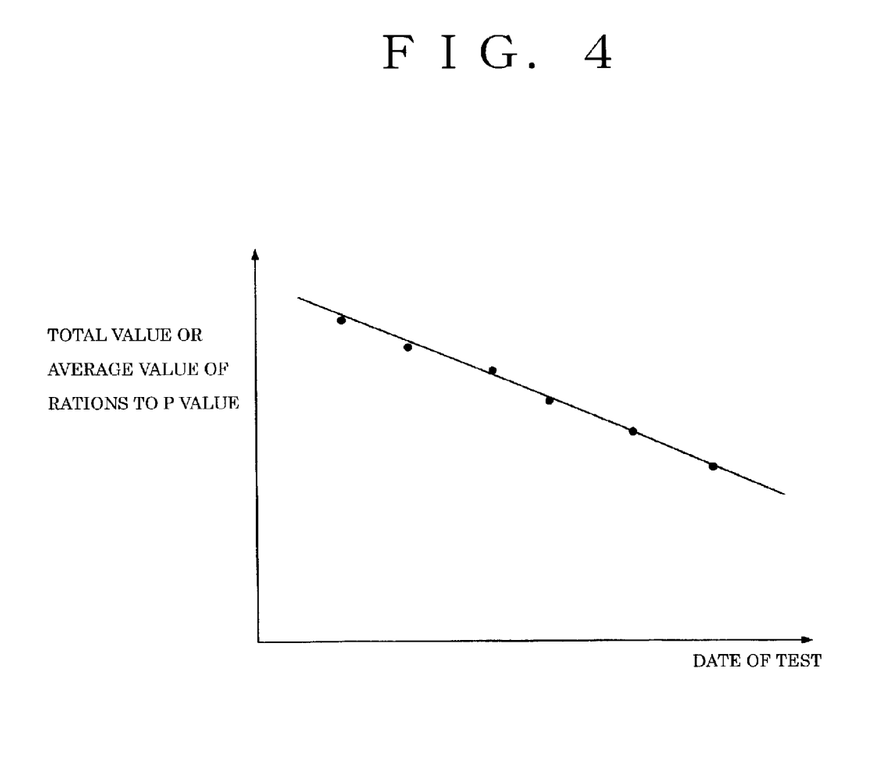
FIG. 4 is a view of an example of a graph outputted through the perimeter according to the invention.

In this case, it is preferable to provide test result storing means 10 that stores the total value or the average value computed by the means for adding ratios to p value 9 as well as examinee ID for identification of the examinee, and change output means 11 for outputting changes with time of the total value or the average value of the examinee, and to show a graph or a table on a printer 12 or a monitor (see FIG. 4).

On the other hand, a method of controlling the perimeter 1 has a step of presenting the stimulus A having predetermined luminance in order to a plurality of positions where the stimulus should be presented through the stimulus presentation means 2;

a step of judging the luminance of the stimulus perceived by the examinee for each position where the stimulus should be presented through the luminance judging means 4 based upon response signals showing that the examinee has perceived the presented stimulus (that is, the response signals from the response means 3) and signals from the stimulus presentation means 2;

a step of computing the sensitivity deviation which is a difference between the value regarding the luminance of the stimulus perceived by the examinee and the normal value through the sensitivity deviation computing means 7 for each position where the stimulus should be presented based upon "the normal value of the luminance of the stimulus to be perceived with normal eyes" that is stored in the normal value storing means 5 as data in connection with each position where each stimulus should be presented and the signals from the luminance judging means 4; and a step of computing "the ratio to p value" that is the ratio between "the p value that is the critical value of the luminance of the stimulus perceived by a predetermined rate of normal eyes" that is stored in the p value storing means 6 as data in connection with each position where the stimulus should be presented and the sensitivity deviation computed by the sensitivity deviation computing means 7 for each position where the stimulus should be presented through means for computing ratio to p value 8; and a step of computing the total value of the ratios top value computed for respective positions where the stimulus should be presented or the average value obtained by dividing the total value by the number of positions where the stimulus should be presented through means for adding ratios to p value 9.

In such a case, the above-mentioned method may have a step of storing the total value or the average value that is computed by means of adding ratios to p value 9 through the test result storing means 10 as well as the examinee ID for identification of each examinee, and a step of outputting the change of the total value or the average value of the examinee with time through change output means 11.

A structure of the stimulus presentation means 2 as shown in FIG. 2 is mentioned briefly.

A reference number 20 in the figure denotes the stimulus presentation portion for presenting stimulus A in the visual field of the examinee, a reference numeral 21 denotes the presentation portion changing portion for changing the portion where the stimulus A is presented and a reference numeral 22 denotes the luminance setting portion for setting the luminance of the stimulus A.

The stimulus presentation portion 20 in the figure is comprised of a projection optical system 20A for projecting stimuli and projection member 20B where stimuli are projected by the projection optical system 20A, but may have any structure as long as the stimulus presentation portion 20 can present the stimuli in the visual field of the examinee. For example, a plurality of LEDs may be located and be selectively lighted. The projection member 20B in FIG. 2 has a semi-spherical dome shape (visual field dome), but may have a shape with a curved face excluding a semi-sphere or a shape with a plane.

If the stimulus presentation portion 20 is comprised of the projection optical system 20A and the projection member 20B as shown in FIG. 2, the presentation portion changing portion 21 may be comprised of driving means for changing positions of structural elements of the projection optical system 20A, such as projector mirrors 211, 212 (not shown). If the stimulus presentation portion is comprised of a plurality of LEDs, which LED should be lighted may be controlled by the presentation portion changing portion. Even if any of the projection optical system and LED is used, an examiner may manually instruct to change the portion to be presented with a touch pen, a mouse or a keyboard, watching a display, or the change of the portion to be presented may be automatically instructed through a program prepared in advance.

The luminance setting portion 22 as shown in FIG. 2 is comprised of turrets 221, 222 having a plurality of filters rotatably supported which attenuation is different and driving mechanism 223 for changing positions of the turrets 221, 222, but may have another structure.

The present invention has been explained on the basis of the example embodiments discussed. Although some variations have been mentioned, the embodiments which are described in the specification are illustrative and not limiting. The scope of the invention is designated by the accompanying claims and is not restricted by the descriptions of the specific embodiments. Accordingly, all the transformations and changes within the scope of the claims are to be construed as included in the scope of the present invention.

The invention claimed is:

1. A perimeter for testing a visual field of an examinee in such a state the examinee fixates a predetermined fixation target, comprising:
    stimulus presentation means for presenting a stimulus having predetermined luminance in order at a plurality of positions where stimulus should be presented in a periphery of said fixation target;
    response means through which an examiner or the examinee inputs response signals showing that the examinee actually perceived the presented stimulus;
    luminance judging means for judging said luminance of said stimulus perceived by the examinee for each position where said stimulus should be presented based upon signals from said stimulus presentation means and said response means;
    representative value storing means for storing "a representative value of the luminance of the stimulus to be perceived with normal eyes" statistically obtained in perimetry that is conducted on a plurality of persons having normal eyes as data in connection with each position where the stimulus should be presented;
    critical value storing means for storing "a critical value that shows a boundary of the luminance of the stimulus perceived by a predetermined rate of normal eyes" statistically obtained in perimetry that is conducted on a plurality of persons having normal eyes as data in connection with each position where the stimulus should be presented;
    sensitivity deviation computing means for computing sensitivity deviation that is a difference between a value in connection with the luminance of the stimulus perceived by the examinee and said representative value for each position where the stimulus should be presented based upon said signals from said luminance judging means and said data of said representative value storing means;
    means for computing ratio to critical value which computes "a ratio to critical value" that is a ratio between a critical value stored in said critical value storing means and said sensitivity deviation computed by said sensitivity deviation computing means for each position where the stimulus should be presented; and
    means for adding ratios to critical value, which computes a total value of said ratios to critical value computed for each position where the stimulus should be presented or an average value obtained by dividing said total value by number of positions where the stimulus should be presented.

2. The perimeter according to claim 1, wherein said representative value is a value determined from a characteristic curve that shows a relation between "the luminance of the stimulus" obtained by conducting perimetry on a plurality of persons having normal eyes and "number of persons who actually perceived the stimulus having the luminance, and is the value based upon the luminance of the stimulus perceived by the most persons, a value based upon an average value obtained by dividing the perceived luminance by a number of said persons, or a value based upon the luminance of the stimulus perceived by almost middle rank of person when said persons are ranked based upon the perceived luminance.

3. The perimeter according to claim 1, further comprising:
    test result storing means for storing said total value or said average value computed by said means for adding ratios to critical value as well as examinee ID for identification of the examinees; and
    change output means for outputting changes with time in the total value or the average value of the examinee.

4. A method of controlling a perimeter, comprising:
    a step of presenting a stimulus having predetermined luminance in order to a plurality of positions where the stimulus should be presented through stimulus presentation means;
    a step of judging the luminance of the stimulus perceived by the examinee for each position where the stimulus should be presented through luminance judging means based upon response signals showing that the examinee has perceived the presented stimulus and signals from the stimulus presentation means;
    a step of computing sensitivity deviation which is a difference between a value regarding the luminance of the stimulus perceived by the examinee and the representative value through sensitivity deviation computing means for each position where the stimulus should be presented based upon "a representative value of the luminance of the stimulus to be perceived with normal eyes" that is stored in representative value storing means as data in connection with each position where each stimulus should be presented and the signals from the luminance judging means;
    a step of computing "a ratio to critical value" that is the ratio between "a critical value that is a boundary of the luminance of the stimulus perceived by a predetermined rate of normal eyes" that is stored in critical value storing means as data in connection with each position where the stimulus should be presented and the sensitivity deviation computed by the sensitivity deviation computing means for each position where the stimulus should be presented through means for computing ratio to critical value; and
    a step of computing a total value of ratios to critical value computed for respective positions where the stimulus should be presented or an average value obtained by dividing the total value by number of positions where the stimulus should be presented through means for adding ratios to critical value.

5. The method of controlling the perimeter according to claim 4, further comprising:
a step of storing the total value or the average value that is computed by means of adding ratios to critical value through the test result storing means as well as the examinee ID for identification of each examinee, and
a step of outputting change of the total value or the average value of the examinee with time through change output means.

* * * * *